United States Patent
Goodwin et al.

(10) Patent No.: US 12,296,308 B2
(45) Date of Patent: May 13, 2025

(54) TUBE MANAGEMENT SYSTEM FOR BIOREACTOR

(71) Applicant: LIFE TECHNOLOGIES CORPORATION, Carlsbad, CA (US)

(72) Inventors: Michael E. Goodwin, Logan, UT (US); Wade A. Cornia, Nibley, UT (US); Jacob D. Lee, Smithfield, UT (US)

( * ) Notice: Subject to any disclaimer, the term of this patent is extended or adjusted under 35 U.S.C. 154(b) by 226 days.

(21) Appl. No.: 17/805,301

(22) Filed: Jun. 3, 2022

(65) Prior Publication Data

US 2022/0288546 A1 Sep. 15, 2022

Related U.S. Application Data

(63) Continuation of application No. 16/196,882, filed on Nov. 20, 2018, now Pat. No. 11,358,107, which is a
(Continued)

(51) Int. Cl.
*B01F 27/88* (2022.01)
*B01F 27/113* (2022.01)
*B01F 27/2121* (2022.01)
*B01F 27/213* (2022.01)
*B01F 27/805* (2022.01)
*B01F 27/85* (2022.01)
(Continued)

(52) U.S. Cl.
CPC .......... *B01F 27/88* (2022.01); *B01F 27/2121* (2022.01); *B01F 27/213* (2022.01); *B01F 27/805* (2022.01); *B01F 27/85* (2022.01); *B01F 33/5012* (2022.01); *B01F 33/5024* (2022.01); *B01F 35/513* (2022.01); *C12M 23/14* (2013.01); *C12M 23/52* (2013.01); *C12M 27/02* (2013.01); *B01F 27/113* (2022.01); *B01F 2101/22* (2022.01)

(58) Field of Classification Search
CPC .......................... B01F 7/1695; B01F 7/00691; B01F 7/00725; B01F 7/1605; B01F 7/1665; B01F 13/003; B01F 13/0042; B01F 15/0085; B01F 7/00341; B01F 2215/0032; C12M 23/14; C12M 23/52; C12M 27/02; C12M 35/04; C12M 21/04; C12M 29/10; C12M 41/00; C12M 29/04; C12M 23/34; C12M 23/06
USPC ....................................... 435/286.7
See application file for complete search history.

(56) References Cited

U.S. PATENT DOCUMENTS 2,589,899 A   3/1952   Vail
3,319,941 A   5/1967   Isaacs, Jr. et al.
(Continued)

OTHER PUBLICATIONS

HyClone User's Guide Brochure, *Single-Use Biroreactor (S.U.B.)50L & 250L*, published at least as early as Jan. 1, 2009.
(Continued)

*Primary Examiner* — Michael L Hobbs
*Assistant Examiner* — Lenora A Abel

(57) ABSTRACT

A tube management system includes an elongated rack extending between a first end and an opposing second end; an elongated first shaft having a first end and an opposing second end, the first shaft being secured to the rack; a securing structure secured to the first shaft; a collapsible bag bounding a chamber; and a tubular member projecting from the collapsible bag, wherein the securing structure at least partially encircles the tubular member.

18 Claims, 15 Drawing Sheets

Related U.S. Application Data continuation of application No. 15/937,610, filed on Mar. 27, 2018, now Pat. No. 10,150,090, which is a continuation of application No. 14/627,780, filed on Feb. 20, 2015, now Pat. No. 9,943,814, which is a continuation of application No. 13/162,248, filed on Jun. 16, 2011, now Pat. No. 8,960,486.

(60) Provisional application No. 61/355,479, filed on Jun. 16, 2010.

(51) Int. Cl.
*B01F 33/501* (2022.01)
*B01F 33/502* (2022.01)
*B01F 35/513* (2022.01)
*B01F 101/22* (2022.01)
*C12M 1/00* (2006.01)
*C12M 1/06* (2006.01)

(56) References Cited

U.S. PATENT DOCUMENTS

| | | | |
|---|---|---|---|
| 3,559,960 A | 2/1971 | Elder et al. | |
| 5,727,878 A | 3/1998 | Sullivan, Jr. | |
| 5,884,130 A | 3/1999 | Tsutsumi et al. | |
| 6,083,587 A | 7/2000 | Smith et al. | |
| 6,245,555 B1 | 6/2001 | Curtis | |
| 6,461,033 B2 * | 10/2002 | Palmer | B01F 33/502 366/67 |
| 6,923,567 B2 | 8/2005 | Bibbo et al. | |
| 7,176,024 B2 * | 2/2007 | Branson | C12M 23/48 47/DIG. 6 |
| 7,384,783 B2 | 6/2008 | Kunas et al. | |
| 7,434,983 B2 | 10/2008 | Terentiev | |
| 7,682,067 B2 | 3/2010 | West et al. | |
| 8,623,640 B2 | 1/2014 | Kunas | |
| 8,690,418 B2 | 4/2014 | Ludwig | |
| 8,960,486 B2 | 2/2015 | Goodwin | |
| 9,943,814 B2 | 4/2018 | Goodwin | |
| 10,150,090 B2 | 12/2018 | Goodwin | |
| 11,358,108 B2 * | 6/2022 | Wang | B01F 35/423 |
| 2002/0131654 A1 | 9/2002 | Smith et al. | |
| 2003/0077466 A1 | 4/2003 | Smith et al. | |
| 2003/0198406 A1 | 10/2003 | Bibbo | |
| 2003/0226857 A1 | 12/2003 | Bibbo | |
| 2003/0231546 A1 | 12/2003 | Bibbo | |
| 2005/0073908 A1 | 4/2005 | Bibbo | |
| 2005/0239199 A1 * | 10/2005 | Kunas | B01F 35/51 435/297.1 |
| 2006/0196501 A1 * | 9/2006 | Bibbo | C12M 23/14 128/200.23 |
| 2006/0240546 A1 | 10/2006 | Goodwin et al. | |
| 2006/0270036 A1 | 11/2006 | Goodwin et al. | |
| 2007/0214899 A1 | 9/2007 | Goodwin | |
| 2009/0196726 A1 | 8/2009 | Campos Del Olmo et al. | |
| 2011/0114651 A1 | 5/2011 | Ottman | |
| 2011/0188928 A1 | 8/2011 | West et al. | |

OTHER PUBLICATIONS

U.S. Appl. No. 13/162,248, filed Jun. 16, 2011.
U.S. Appl. No. 14/627,780, filed Feb. 20, 2015.
U.S. Appl. No. 15/937,610, filed Mar. 27, 2018.
U.S. Appl. No. 16/196,882, filed Nov. 20, 2018.

* cited by examiner

TUBE MANAGEMENT SYSTEM FOR BIOREACTOR

CROSS-REFERENCE TO RELATED APPLICATIONS

This application is a continuation of U.S. patent application Ser. No. 16/196,882, filed Nov. 20, 2018, now U.S. Pat. No. 11,358,107, which is a continuation of U.S. patent application Ser. No. 15/937,610, filed Mar. 27, 2018, now U.S. Pat. No. 10,150,090, which is a continuation U.S. patent application Ser. No. 14/627,780, filed Feb. 20, 2015, now U.S. Pat. No. 9,943,814, which is a continuation of U.S. patent application Ser. No. 13/162,248, filed Jun. 16, 2011, now U.S. Pat. No. 8,960,486, which claims the benefit of U.S. Provisional Application No. 61/355,479, filed Jun. 16, 2010, which are incorporated herein by specific reference.

BACKGROUND OF THE INVENTION

1. The Field of the Invention

The present invention relates to bioreactor systems and, more specifically, to bioreactor systems with supports for tubes and probes.

2. The Relevant Technology

The biopharmaceutical industry uses a broad range of mixing systems for a variety of processes such as in the preparation of media and buffers. The mixing systems can also be in the form of bioreactors or fermentors for growing of cells or microorganisms. Some current mixing systems include a rigid housing in which a flexible bag is positioned. The bag is filled with the desired fluid for mixing and an impeller disposed within the bag is used to mix the fluid. Depending on the fluid being processed, there are typically fluid lines and different sensors and/or probes coupled with the bag. Where a number of fluid lines, probes, and sensors are being used, the lines, probes, and sensors can be difficult to organize and control. Furthermore, some probes and sensors must be held stationary at a specified angle to operate properly.

In one attempt to organize and control fluid lines, probes and sensors, a tray has been mounted to the rigid housing. The tray is designed to sit at a predefined angle and the lines, probes, and sensors can be secured to the tray. Although the trays are useful, they have some shortcomings. For example, the trays are relatively large and outwardly project from the rigid housing. As such, the trays can be an obstruction to those operating around the rigid housing. Likewise, the trays can obstruct the view or access to items located below the trays. In addition, the trays can limit the ability to access and manipulate lines, probes and sensors located between other lines, probes and sensors.

Accordingly, what is needed in the art are mixing systems having an improved ability to organize and control fluid line, probes, and/or sensors extending from fluid bags.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for mixing and, if desired, sparging solutions and/or suspensions. The systems can be commonly used as bioreactors or fermenters for culturing cells or microorganisms. By way of example and not by limitation, the inventive systems can be used in culturing bacteria, fungi, algae, plant cells, animal cells, protozoans, nematodes, and the like. The systems can accommodate cells and microorganisms that are aerobic or anaerobic and are adherent or non-adherent. The systems can also be used in association with the formation and/or treatment of solutions and/or suspensions that are not biological but nevertheless incorporate mixing and, if desired, sparging. For example, the systems can be used in the formation of media where sparging is used to control the pH of the media through adjustment of the carbonate/bicarbonate levels with controlled gaseous levels of carbon dioxide. The systems can also be used for mixing powders or other components into a liquid where sparging is not required.

The inventive systems are designed so that a majority of the system components that contact the material being processed can be disposed of after each use. As a result, the inventive systems substantially eliminate the burden of cleaning and sterilization required by conventional stainless steel mixing systems. This feature also ensures that sterility can be consistently maintained during repeated processing of multiple batches. The inventive systems are also adjustable so that they can be used for mixing a variety of different batch sizes. In view of the foregoing, and the fact that the inventive systems are easily scalable, relatively low cost, and easily operated, the inventive systems can be used in a variety of industrial and research facilities that previously outsourced such processing.

Figure 1:
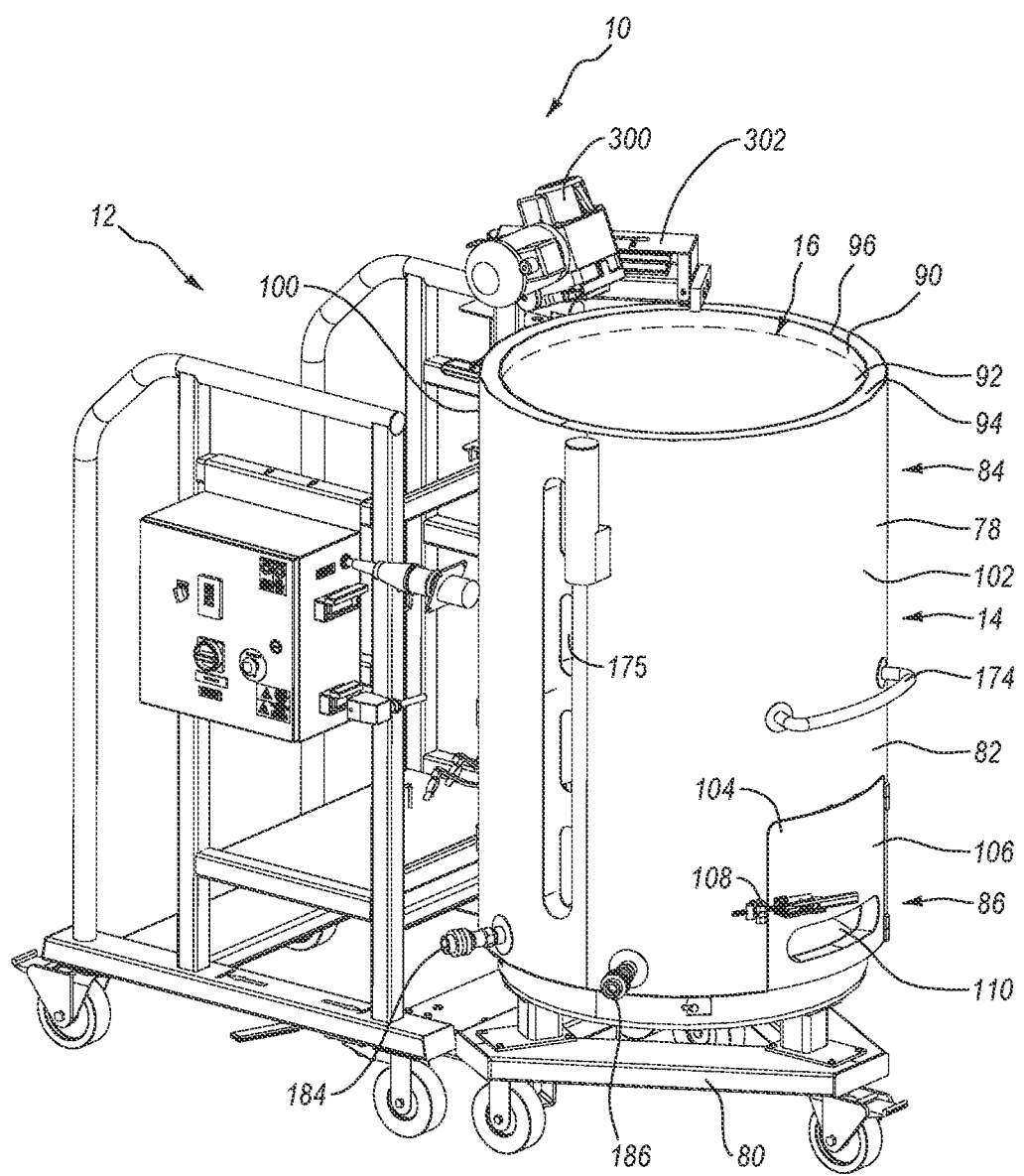
FIG. 1 is a perspective view of a container station docked with a docking station.

Depicted in FIG. 1 is one embodiment of an inventive system 10 incorporating features of the present invention. In general, system 10 comprises a docking station 12, a container station 14 that removably docks with docketing station 12, a container assembly 16 (FIG. 2) that is supported by container station 14, and a drive shaft 362 (FIG. 3) that extends between docking station 12 and container assembly 16. Container assembly 16 houses the solution or suspension that is mixed. The various components of system 10 will now be discussed in greater detail.

Figure 2:
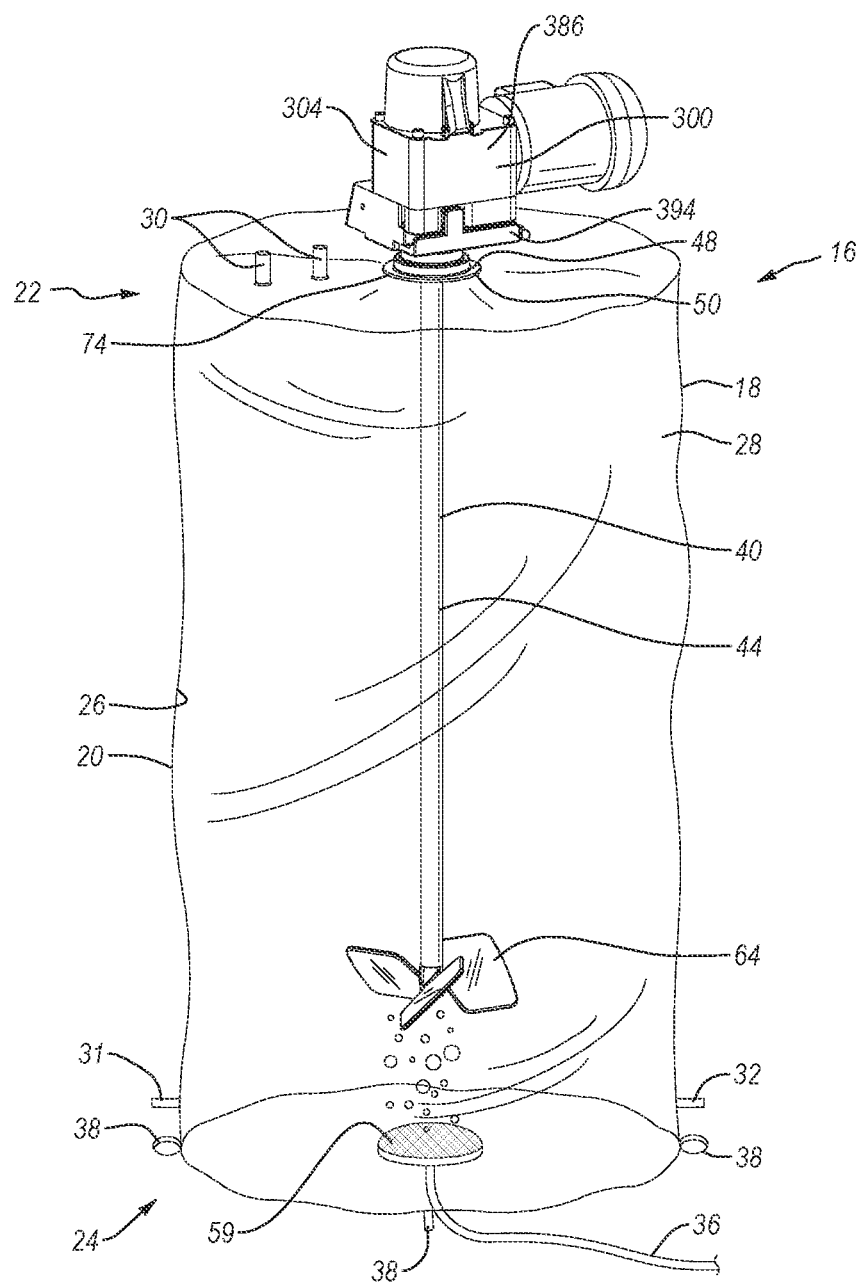
FIG. 2 is a perspective view of a container assembly that is used with the container station shown in FIG. 1.

As depicted in FIG. 2, container assembly 16 comprises a container 18 having a side 20 that extends from an upper end 22 to an opposing lower end 24. Container 18 also has an interior surface 26 that bounds a compartment 28. Compartment 28 is configured to hold a fluid. In the embodiment depicted, container 18 comprises a flexible bag that is comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present invention is the Thermo Scientific CX3-9 film available from Life Technologies Corporation. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Life Technologies Corporation. The Thermo Scientific CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by Life Technologies Corporation as the Thermo Scientific BM1 film) while the outer barrier web is a 5.5 mil thick 6-layer coextrusion film (which is referred to by Life Technologies Corporation as the Thermo Scientific BX6 film).

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003 which are hereby incorporated by specific reference.

In one embodiment, container 18 comprises a two-dimensional pillow style bag wherein two sheets of material are placed in overlapping relation and the two sheets are bonded together at their peripheries to form the internal compartment. Alternatively, a single sheet of material can be folded over and seamed around the periphery to form the internal compartment. In another embodiment, the containers can be formed from a continuous tubular extrusion of polymeric material that is cut to length and is seamed closed at the ends.

In still other embodiments, container 18 can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel is substantially identical and comprises a portion of the side wall, top end wall, and bottom end wall of the container. Corresponding perimeter edges of each panel are seamed. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1 that was published Sep. 19, 2002 of which the drawings and Detailed Description are hereby incorporated by reference.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. Although container 18 can be any shape, in one embodiment container 18 is specifically configured to be complementary or substantially complementary to the chamber on container station 14 in which container 18 is received, as will be discussed below.

In any embodiment, however, it is desirable that when container 18 is received within the chamber on container station 14, container 18 is at least generally uniformly supported by container station 14. Having at least general uniform support of container 18 by container station 14 helps to preclude failure of container 18 by hydraulic forces applied to container 18 when filled with fluid.

Although in the above discussed embodiment container 18 has a flexible, bag-like configuration, in alternative embodiments it is appreciated that container 18 can comprise any form of collapsible container or semi-rigid container. Container 18 can also be transparent or opaque and can have ultraviolet light inhibitors incorporated therein.

Continuing with FIG. 2, formed on container 18 are a plurality of ports 30 at upper end 22 and a plurality of ports 31 and 32 on opposing sides of side 20 at lower end 24. Each of ports 30-32 communicate with compartment 28. Although only a few ports 30-32 are shown, it is appreciated that container 18 can be formed with any desired number of ports 30-32 and that ports 30-32 can be formed at any desired location on container 18. Ports 30-32 can be the same configuration or different configurations and can be used for a variety of different purposes. For example, ports 30 can be coupled with fluid lines for delivering media, cell cultures, and/or other components into container 18 and withdrawing gas from container 18. Ports 31 and/or 32 can be useful in withdrawing fluid from container 18 or can have other purposes.

Ports 30-32 can also be used for coupling probes to container 18. For example, when container 18 is used as a bioreactor for growing cells or microorganisms, ports 30-32 can be used for coupling probes such as temperature probes, pH probes, dissolved oxygen probes, and the like. Examples of ports 30-32 and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 30-32 can also be used for coupling container 18 to secondary containers, to condenser systems, and to other desired fittings.

As also shown in FIG. 2, container assembly 16 can comprise a plurality of radially spaced apart looped tabs 38 projecting from lower end 24 of container 18. As discussed below in greater detail, tabs 38 can be used for proper positing of container assembly 16 within container assembly 14.

In one embodiment of the present invention, container assembly 16 includes means for delivering a gas into the lower end of container 18. By way of example and not by limitation, container assembly 16 can comprise a sparger 34 positioned either on or mounted to lower end 24 of container 18 for delivering a gas to the fluid within container 18. As is understood by those skilled in the art, various gases are typically required in the growth of cells or microorganisms within container 18. The gas typically comprises air that is selectively combined with oxygen, carbon dioxide and/or nitrogen. However, other gases can also be used. The addition of these gases can be used to regulate the dissolved oxygen content and pH of a culture. A gas line 36 is coupled with sparger 34 for delivering the desired gas to sparger 34. Gas line 36 need not pass through lower end 24 of container 18 but can extend down from upper end 22 or from other locations.

Sparger 34 can have a variety of different configurations. For example, sparger 34 can comprise a permeable membrane or a fritted structure comprised of metal, plastic or other materials that dispense the gas in small bubbles into container 18. Smaller bubbles can permit better absorption of the gas into the fluid. In other embodiments, sparger 34 can simply comprise a tube, port, or other type opening formed on or coupled with container 18 through which gas is passed into container 18. In contrast to being disposed on container 18, the sparger can also be formed on or coupled with impeller 64 which is discussed below. Examples of spargers and how they can be used in the present invention are disclosed in United States Patent Publication Nos. 2006/0270036 and 2006/0240546 which were previously incorporated by reference. Other conventional spargers can also be used.

Figure 3:
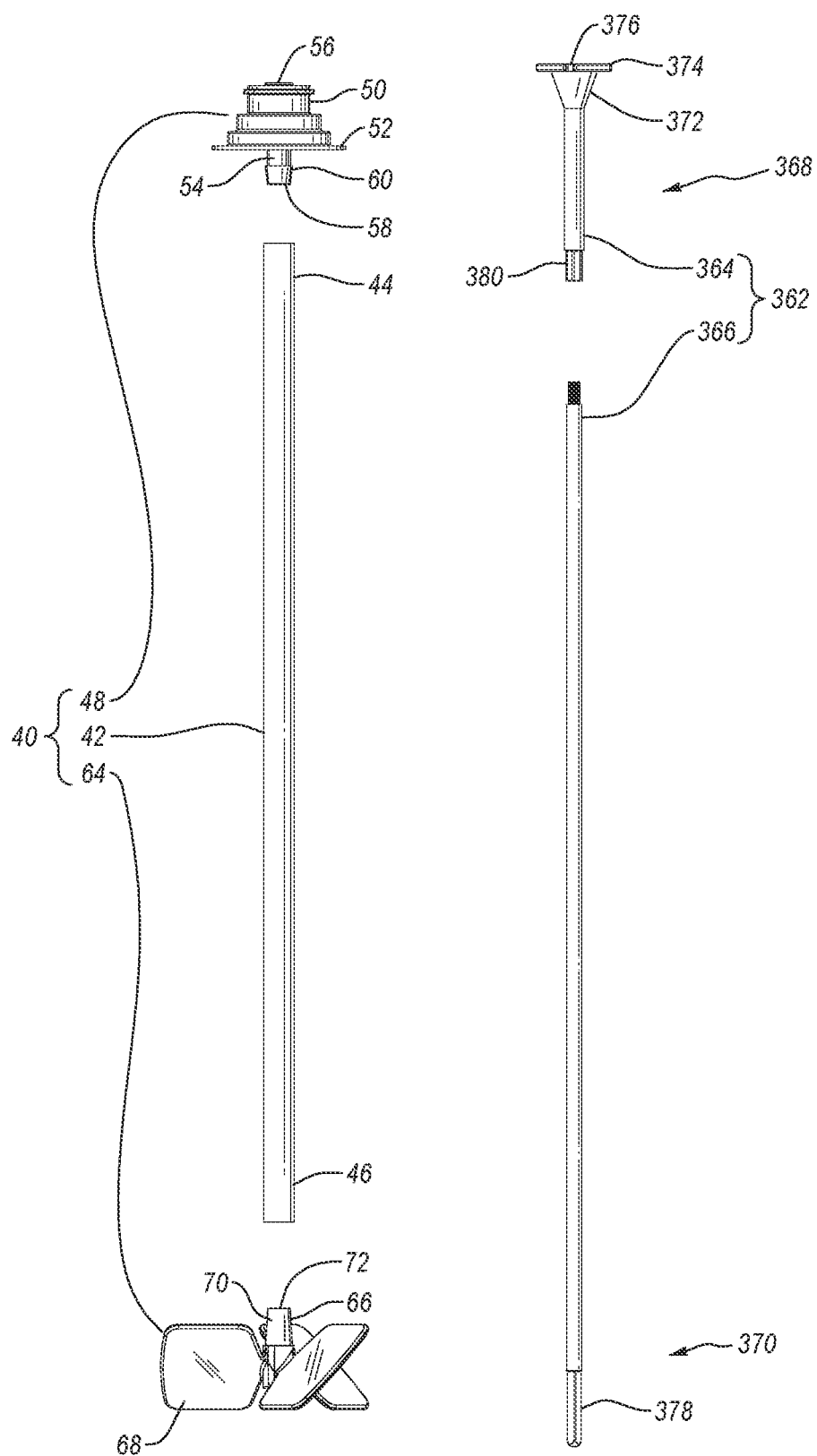
FIG. 3 is an elevated side view of an impeller assembly forming part of the container assembly shown in FIG. 2 and a drive shaft.

Container assembly 16 further comprises an impeller assembly 40. As depicted in FIG. 3, impeller assembly 40 comprises an elongated tubular connector 44 having a rotational assembly 48 mounted at one end and an impeller 64 mounted on the opposing end. More specifically, tubular connector 44 has a first end 46 and an opposing second end 48 with a passage 50 that extends therebetween. In one embodiment, tubular connector 44 comprises a flexible tube such as a polymeric tube. In other embodiments, tubular connector 44 can comprise a rigid tube or other tubular structure.

Rotational assembly 48 is mounted to first end 46 of tubular connector 44. Rotational assembly 48 comprises an outer casing 50 having an outwardly projecting flange 52 and a tubular hub 54 rotatably disposed within outer casing 50. A bearing assembly can be disposed between outer casing 50 and tubular hub 54 to permit free and easy rotation of hub 54 relative to casing 50. Likewise, one or more seals can be formed between outer casing 50 and tubular hub 54 so that during use an aseptic seal can be maintained between outer casing 50 and tubular hub 54 as tubular hub 54 rotates relative to outer casing 50.

Hub 54 has an interior surface 56 that bounds an opening 58 extending therethrough. As will be discussed below in greater detail, an engaging portion of interior surface 56 has a polygonal or other non-circular transverse cross section so that a driver portion of drive shaft 362 passing through opening 58 can engage the engaging portion and facilitate rotation of hub 54 by rotation of drive shaft 362. Hub 54 can also comprise a tubular stem 60 projecting away from outer casing 50. Hub 54 can couple with first end 44 of tubular connector 42 by stem 60 being received within first end 44. A pull tie, clamp, crimp or other fastener can then be used to further secure stem 60 to tubular connector 42 so that a liquid tight seal is formed therebetween. Other conventional connecting techniques can also be used.

Impeller 64 comprises a central hub 66 having a plurality of fins 68 radially outwardly projecting therefrom. It is appreciated that a variety of different numbers and configurations of fins 68 can be mounted on hub 66. Hub 66 has a first end 70 with a blind socket 72 formed thereat. Socket 72 typically has a noncircular transverse cross section, such as polygonal, so that it can engage a driver portion of drive shaft 362. Accordingly, as will be discussed below in greater detail, when a driver portion is received within socket 72, the driver portion engages with impeller 64 such that rotation of drive shaft 362 facilities rotation of impeller 64.

In one embodiment, hub 66 and fins 68 of impeller 64 are molded from a polymeric material. In alternative embodiments, hub and fins 68 can be made of metal, composite, or a variety of other materials. If desired, an annular insert can be positioned within socket 72 to help reinforce hub 66. For example, the insert can be comprised of metal or other material having a strength property greater than the material from which hub 66 is comprised.

Impeller 64 can be attached to connector 42 by inserting first end 70 of hub 66 within connector 42 at second end 46. A pull tie, clamp, crimp, or other type of fastener can then be cinched around second end 46 of connector 42 so as to form a liquid tight sealed engagement between impeller 64 and connector 42.

Returning to FIG. 2, rotational assembly 48 is secured to container 18 so that tubular connector 42 and impeller 64 extend into or are disposed within compartment 28 of container 18. Specifically, in the depicted embodiment container 12 has an opening 74 at upper end 22. Flange 52 of outer casing 50 is sealed around the perimeter edge bounding opening 74 so that hub 54 is aligned with opening 74. Tubular connector 42 having impeller 64 mounted on the end thereof projects from hub 54 into compartment 28 of container 18. In this configuration, outer casing 50 is fixed to container 18 but hub 54, and thus also tubular connector 42 and impeller 64, can freely rotate relative to outer casing 50 and container 18. As a result of rotational assembly 48 sealing opening 74, compartment 28 is sealed closed so that it can be used in processing sterile fluids.

As depicted in FIG. 3, impeller assembly 40 is used in conjunction with a drive shaft 362. In general drive shaft 362 comprises a head section 364 and a shaft section 366 that can be coupled together by threaded connection or other techniques. Alternatively, drive shaft 362 can be formed as a single piece member or from a plurality of attachable sections. Drive shaft 362 has a first end 368 and an opposing second end 370. Formed at first end 368 is a frustoconical engaging portion 372 that terminates at a circular plate 374. Notches 376 are formed on the perimeter edge of circular plate 374 and are used for engaging drive shaft 362 with a drive motor assembly as will be discussed below.

Formed a second end 370 of drive shaft 362 is a driver portion 378. Driver portion 378 has a noncircular transverse cross section so that it can facilitate locking engagement within hub 66 of impeller 64. In the embodiment depicted, driver portion 378 has a polygonal transverse cross section. However, other noncircular shapes can also be used. A driver portion 378 is also formed a long drive shaft 362 toward first end 368. Driver portion 380 also has a noncircular transverse cross section and is positioned so that it can facilitate locking engagement within the interior surface of hub 54 of rotational assembly 48.

During use, as will be discussed below in further detail, drive shaft 362 is advanced down through hub 54 of rotational assembly 48, through tubular connecter 42 and into hub 66 of impeller 64. As a result of the interlocking engagement of driver portions 378 and 380 with hubs 66 and 54, respectively, rotation of drive shaft 362 by a drive motor assembly facilitates rotation of hub 54, tubular connecter 42 and impeller 64 relative to outer casing 50 of rotational assembly 48. As a result of the rotation of impeller 64, fluid within container 18 is mixed.

It is appreciated that impeller assembly 40, drive shaft 362 and the discrete components thereof can have a variety of different configuration and can be made of a variety of different materials. Alternative embodiments of and further disclosure with respect to impeller assembly 40, drive shaft 362, and the components thereof are disclosed in US Patent Publication No. 2011/0188928, published Aug. 4, 2011 which is incorporated herein in its entirety by specific reference.

Returning to FIG. 1, container station 14 comprises a support housing 78 supported on a cart 80. Support housing 78 has a substantially cylindrical sidewall 82 that extends between an upper end 84 and an opposing lower end 86. Lower end 86 has a floor 88 (FIG. 6) mounted thereto. As a result, support housing 14 has an interior surface 90 that bounds a chamber 92. An annular lip 94 is formed at upper end 84 and bounds an opening 96 to chamber 92. As discussed above, chamber 92 is configured to receive container assembly 16 so that container 18 is supported therein.

Although support housing 78 is shown as having a substantially cylindrical configuration, in alternative embodiments support housing 78 can have any desired shape capable of at least partially bounding a compartment. For example, sidewall 82 need not be cylindrical but can have a variety of other transverse, cross sectional configurations such as polygonal, elliptical, or irregular. Furthermore, it is appreciated that support housing 78 can be scaled to any desired size. For example, it is envisioned that support housing 78 can be sized so that chamber 92 can hold a volume of less than 50 liters, more than 1,000 liters or any of the other volumes as discussed above with regard to container 18. Support housing 78 is typically made of metal, such as stainless steel, but can also be made of other materials capable of withstanding the applied loads of the present invention.

With continued reference to FIG. 1, sidewall 82 of support housing 78 has a first side face 100 and an opposing second side face 102. An enlarged access 104 is formed on second side face 102 at lower end 86 so as to extend through sidewall 82. A door 106 is hingedly mounted to sidewall 82 and can selectively pivot to open and close access 104. A latch assembly 108 is used to lock door 106 in the closed position. An opening 110, which is depicted in the form of an elongated slot, extends through an elongated slot, extends through door 106. Opening 110 is configured to align with ports 32 (FIG. 2) of container assembly 16 when container assembly 14 is received within chamber 92 so that ports 32 project into or can otherwise be accessed through opening 110. In some embodiments, a line for carrying fluid or gas will be couple with port 32 and can extend out of chamber 29 through opening 110. As previously mentioned, any number of ports 32 can be formed on container 18 and thus a number of separated lines may pass out through opening 110. Alternatively, different types of probes, inserts, connectors or the like may be coupled with ports 32 which can be accessed through opening 110.

Figure 4:
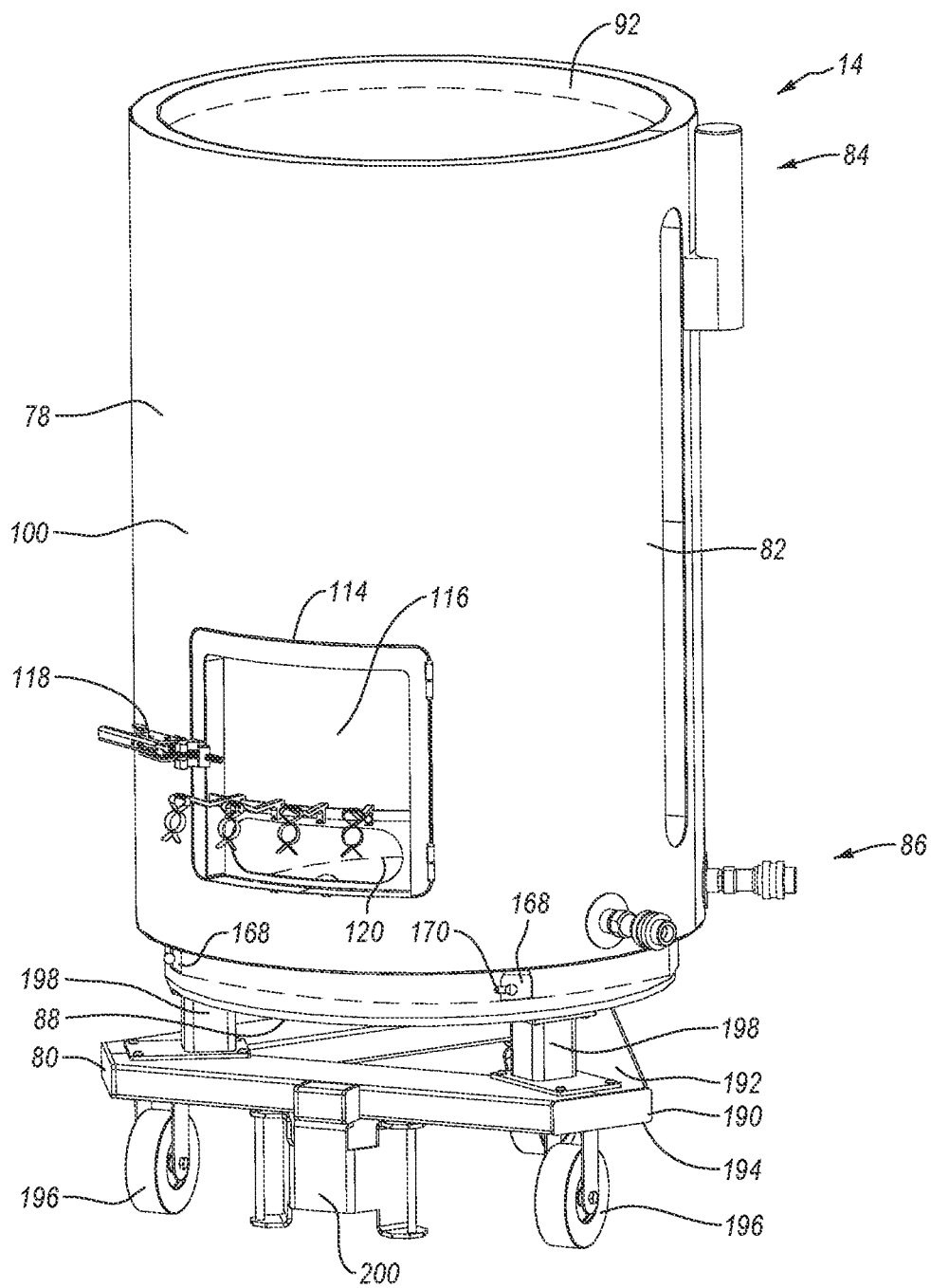
FIG. 4 is a front perspective view of the container station shown in FIG. 1.

Turning to FIG. 4, similar to second side face 102, an enlarged access 114 is formed on first side face 100 at lower end 86 so as to extend through sidewall 82. A door 116 is hingedly mounted to sidewall 82 and can selectively pivot to open and close access 114. A latch assembly 118 is used to lock door 116 in the closed position. An opening 120, which is depicted in the form of an elongated slot, extends through door 116. Opening 120 is configured to align with ports 32 (FIG. 2) of container assembly 16 when container assembly 14 is received within chamber 92 and serves the same corresponding function as discussed above with regard to opening 110.

Figure 5:
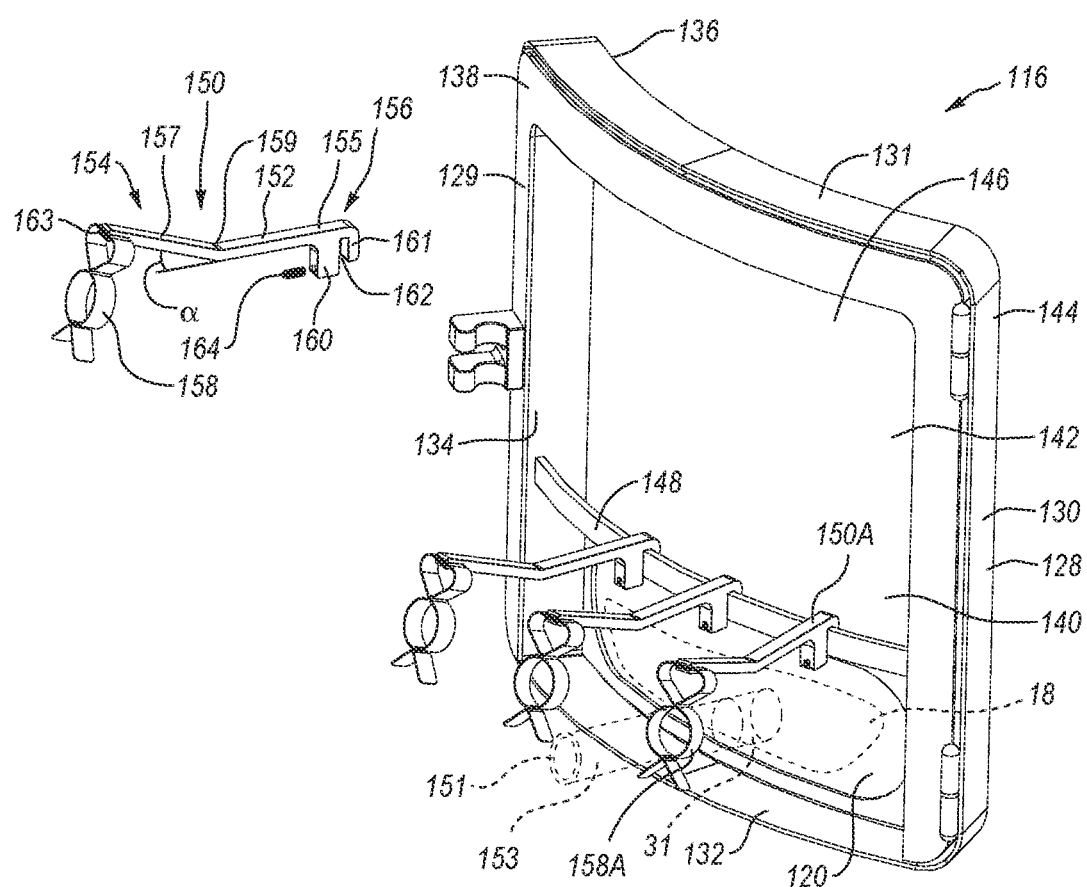
FIG. 5 is a perspective view of a door of the container station shown in FIG. 4.

As shown in FIG. 1, door 106 has an exterior surface 107 that is substantially flush with the exterior surface of side wall 82 when door 106 is in the closed position. In contrast, as shown in FIG. 5, door 116 has a perimeter frame 128 that includes a first side rail 129, a spaced part second side rail 130, an upper rail 131 that extends between the upper ends of rails 129 and 130, and a lower rail 132 that extends between the lower ends of rails 129 and 130. Each of rails 129-132 has an inside face 134 that extends between an interior surface 136 and an exterior surface 138. Door 106 further includes a panel 140 having a front face 142 and an opposing back face 144. Panel 140 is mounted on or adjacent to inside face 134 of rails 129-132 so that back face 144 of panel 140 is disposed substantially flush with interior surface 80 of support housing 78 when door 116 is in the closed position. Panel 140 has opening 120 extending therethrough. As a result of the position of panel 140, a recess 146 is formed on door 106 that is bounded in part by front face 142 of panel 140 and inside face 134 of rails 129-132.

An elongated rack 148 is connected to and extends between inside faces 134 of side rails 129 and 130 so that rack 148 is retained within recess 146. In the depicted embodiment rack 148 comprises a flat bar that is curved along the length thereof. Alternatively, other support structures can also be used. For example, rack 148 can have a transverse cross section that is circular, polygonal or other configurations. Rack 148 is positioned so as to be slightly above or aligned with opening 120. Rack 148 is disposed within recess 146 to help protect it from damage during movement, shipping or use of container station 14. In alternative embodiments, rack 148 can project outside of recess 146, can be mounted on exterior faces of rails 129 and 130 or can be formed in a generally elongated U-shaped configuration and mounted on the exterior surface of door 106.

Rack 148 is used to support one or more removable hangers 150. As shown in FIG. 5, each hanger 150 comprises an elongated shaft 152 having a first end 154 and an opposing second end 156. As depicted, shaft 152 upwardly bends at a location between opposing ends 154 and 156. More specifically, shaft 152 has a first shaft section 155 that includes first end 154 and a second shaft section 157 that includes second end 156. First shaft section 155 and second shaft section 157 join at an intersection 159. Second shaft section 157 slopes up and away from first shaft section 155 so that an angle α is formed between a long axis of first shaft section 155, which can be horizontal, and a long axis of second shaft section 157. Angle α typically has a range between about 5° to about 25° with about 5° to about 15° being more common.

Mounted at first end 154 of shaft 152 is a conventional hose clamp 158. In the depicted embodiment, a slot 163 is formed at first end 154 and hose clamp 158 is slidably received therein for engaging with shaft 152. Hose clamp 158 comprises a pair of resiliently flexible arms that can be manually pried apart. Once the hose is positioned between the arms, the arms resiliently press back toward each other so as to secure the hose therebetween. Other hose clamps or other structures capable of holding or securing a hose can also be used.

Downwardly projecting from second end 156 of shaft 152 is a pair of spaced apart rigid arms 160 and 161 that bound a slot 162 therebetween. Hanger 150 is attached to rack 148 by sliding rack 148 into slot 162. A set screw 164 can then be threaded through arm 160 to bias against rack 148 so as to secure hanger 150 to rack 148. By using this configuration, hanger 150 can be positioned at any location along rack 148 and can be slidably moved along rack 148. Other conventional mounting structures can also be used for removably securing hanger 150 to rack 148.

Hangers 150 are used for supporting hoses that extend out of opening 120 and are coupled with corresponding ports 31 (FIG. 2). Hangers 150 help keep the hoses organized and prevent unwanted kinking. Hangers 150 can also be used for supporting probes, sensors and other structures, as discussed above, that couple with ports 31 projecting out of opening 120. In part, hangers 150 are angled as discussed above because some probes and sensors are designed to be held at a constant angle relative to the horizontal to enable proper operation. The angle of hangers 150 also facilitates ease in inspection, attachment, and removal of hoses, probes, sensors and the like.

It is appreciated that any number of hangers 150 can be attached to rack 148. During shipping or movement of container station 14, hangers 150 can be removed so that they are not damaged and do not form an obstruction. Hangers 150 also have the advantage of being small. As such, the hangers are a minimal obstruction to those operating around support housing 78 and provide minimal obstruction to structures that may be located below the hangers, such as other probes, sensors, or tubes. Likewise, the number of hangers used can be limited to the number of hangers, thereby avoiding unnecessary obstructions. In addition, the small discrete hangers make it easy to operate with and adjust multiple hoses, sensors, and/or probes communicating through opening 110.

Accesses 104 and 114 (FIGS. 1 and 4) are in part provided so that when container assembly 16 is being inserted within chamber 92, an operator can reach into chamber 92 through access 104 and/or 114 to help orientate and secure container assembly 16 within chamber 92 and to help align and/or feed various ports and tubes extends from container assembly 16 with or through corresponding openings 110, 120, and the like on support housing 78. In alternative embodiments, it is appreciated that door 106 can be used on both accesses 104 and 114 or that door 116 can be used on both access 104 and 114. In other embodiments, support housing 78 can be formed with only one of access 104 or 114 or that both access 104 and 114 can be eliminated and opening 110 and/or 120 can be formed directly on sidewall 82. In this embodiment, rack 148 can be U-shaped and mounted directly to sidewall 82 adjacent to opening 120.

Returning to FIG. 4, a plurality of radially spaced apart alignment openings 168 extend through sidewall 82 of support housing 78 at lower end 86. A catch 170 laterally projects from an exterior surface of sidewall 82 into alignment with each alignment opening 168. As container assembly 16 is being inserted into chamber 92 of support housing 78, before it is filled with fluid, container 18 is spread apart and looped tabs 38 (FIG. 2) of container assembly 16 are advanced through corresponding alignment openings 168 and secured to a corresponding catch 170. This positioning helps ensure that container assembly 16 is properly positioned and spread apart so that container 18 fully and properly expands during filling with fluid as opposed to parts of container 18 being kinked or remaining folded during filling. It is appreciated that catches 170 can have a variety of different configuration and can also be in the form of straps, elastic cords or the like that can engage and sure tabs 39 to container station 14.

As shown in FIG. 1, support housing 78 can also comprise a handle 174 attached to an outwardly extending sidewall 82. Handle 174 is shown having an elongated U-shaped configuration but can also have other designs. A plurality of vertically aligned observation slots 175 extend along the height of sidewall 82 and extend through sidewall 82 so as to communicate with chamber 92. Observation slots 175 permit and easy verification of the level of fluid within container 18.

Figure 6:
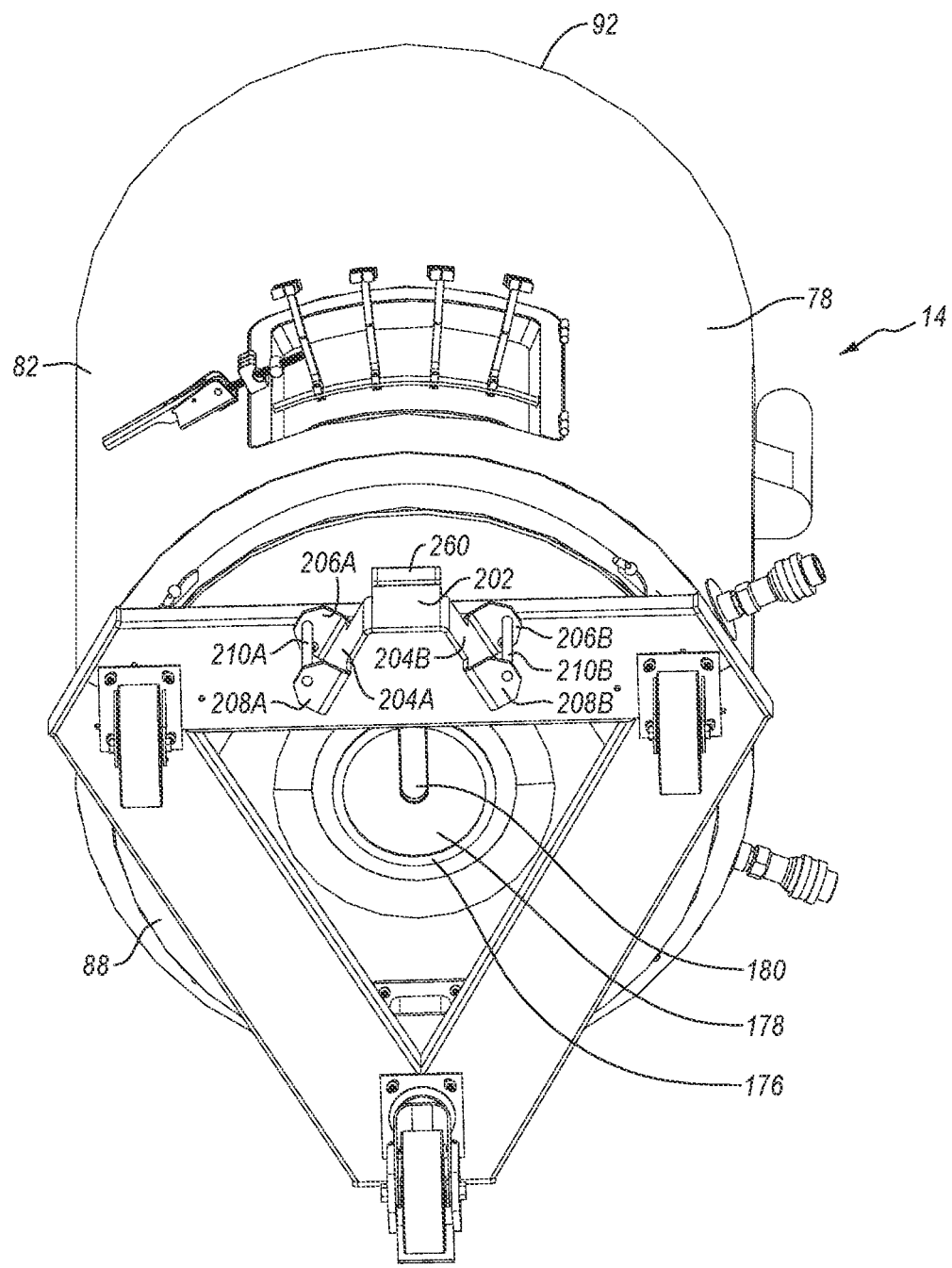
FIG. 6 is a bottom perspective view of the container station shown in FIG. 4.

Turning to FIG. 6, floor 88 of support housing 78 has an enlarged central opening 176 into which a plate 178 is removably positioned. Plate 178 has a slot 180 that extends from a perimeter edge of plate 178 toward a center of plate 178. As such, plate 178 has a generally C-shaped configuration. Plate 178 typically freely sits on floor 88 and can be removed by being pushed up into chamber 92. During use, as container assembly 16 is lowered into chamber 92, a user can push plate 178 out of opening 176 and reach up through opening 176 to grasp gas line 36. Gas line 36 is then pulled down through opening 176 and sparger 34 (FIG. 2) is directed towards opening 176. Finally, gas line 36 passes into slot 180 and plate 178 is fitted within opening 176 so that sparger 34 rests on or is disposed adjacent to plate 178.

In one embodiment of the present invention means are provided for regulating the temperature of the fluid that is contained within container 18 when container 18 is disposed within support housing 78. By way of example and not by limitation, sidewall 82 can be jacketed so as to bound one or more fluid channels that encircle sidewall 82 and that communicate with an inlet port 184 and an outlet port 186. A fluid, such as water or propylene glycol, can be pumped into the fluid channel through inlet port 184. The fluid then flows in pattern around sidewall 82 and then exits out through outlet port 186.

By heating or otherwise controlling the temperature of the fluid that is passed into the fluid channel, the temperature of support housing 78 can be regulated which in turn regulates the temperature of the fluid within container 18 when container 18 is disposed within support housing 78. In an alternative embodiment, electrical heating elements can be mounted on or within support housing 78. The heat from the heating elements is transferred either directly or indirectly to container 18. Alternatively, other conventional means can also be used such as by applying gas burners to support housing 78 or pumping the fluid out of container 18, heating the fluid and then pumping the fluid back into container 18. When using container 18 as part of a bioreactor or fermenter, the means for heating can be used to heat the culture within container 18 to a temperature in a range between about 30° C. to about 40° C. Other temperatures can also be used.

Returning to FIG. 4, cart 80 comprises a platform 190 having a top surface 192 and an opposing bottom surface 194. In the depicted embodiment, platform 190 has a substantially triangular configuration. In alternative embodiments, however, platform 190 can be square, rectangular, circular, or of other polygonal or irregular configurations. Downwardly projecting from bottom surface 194 are a plurality of spaced apart wheels 196. A plurality of spaced apart legs 198 extend between floor 88 of support housing 78 and top surface 192 of platform 190. Legs 198 provide an open gap between support housing 78 and platform 190 so as to enable access to plate 178 (FIG. 6) as previously discussed.

Attached to and downwardly projecting from platform 190 is a locking catch 200. As perhaps better depicted in FIG. 6, locking catch 200 comprises a vertically extending face plate 202 and a pair of arms 204A and 204B project back from opposing sides of face plate 202 in complementary diverging angles so as to extend a generally V-shaped orientation. Arm 204A has a first flange 206A and an second flange 208A orthogonally projecting from opposing upper and lower ends of arms 204A so as to be disposed in substantially parallel planes. An engagement rod 210A is secured to and extends between flanges 206A and 206B at a spaced apart location from arm 204A. Similarly, flanges 206B and 208B extend from opposing upper and lower ends of arm 204B and have an engagement rod 210B extending therebetween. The operation and function of locking catch 200 will be discussed below in greater detail with regard to docking station 12.

Figure 7:
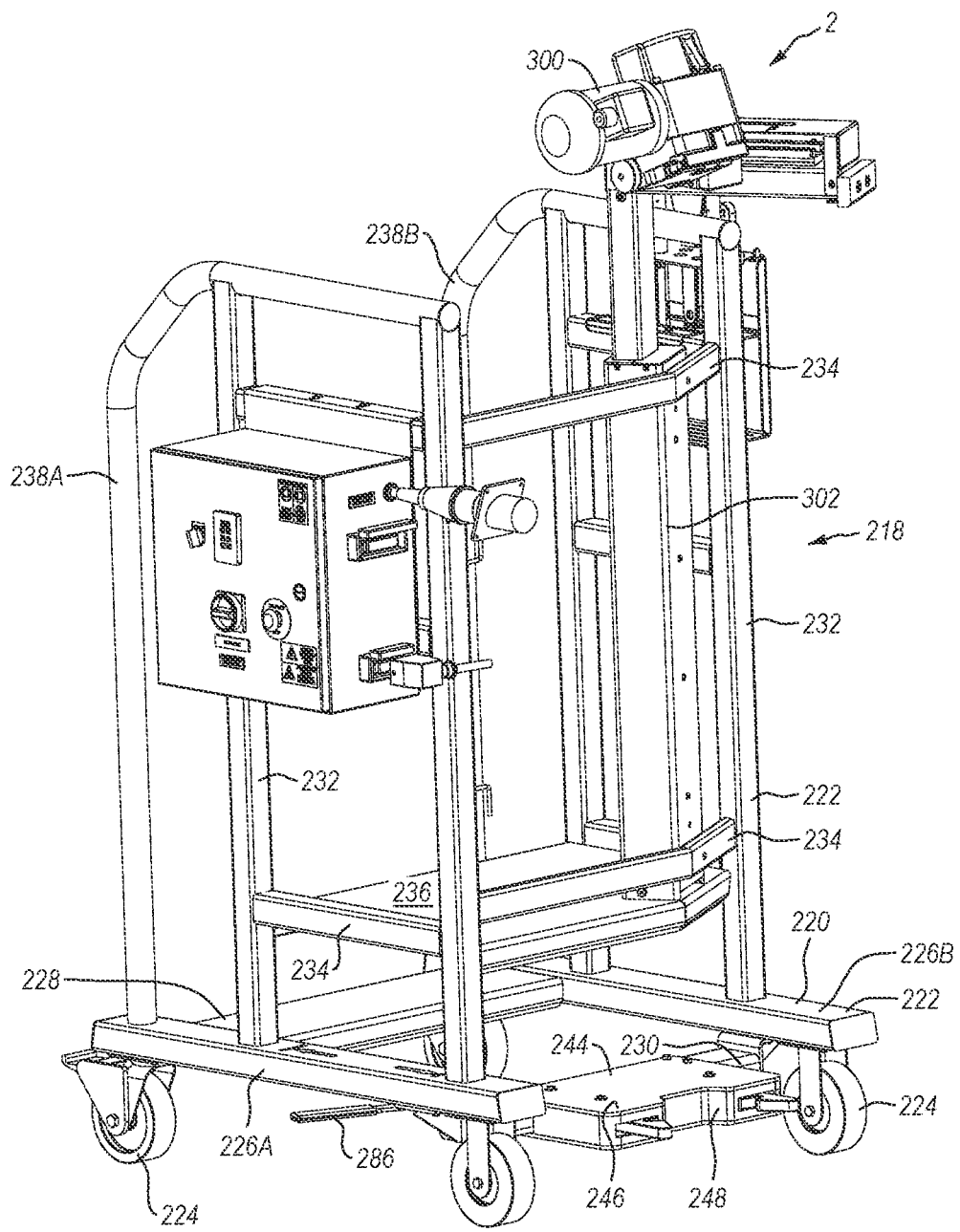
FIG. 7 is a front perspective view of the docking station shown in FIG. 1.

As depicted in FIG. 7, docking station 12 comprises stand 218 which includes a base 220 having a frame assembly 222 upstanding therefrom and a plurality of wheels 224 downwardly projecting therefrom. More specifically, base 220 comprises a pair of spaced apart runners 226A and 226B extending in parallel alignment. A first cross member 228 extends between runners 226A and 226B at a rearward end thereof while a second cross member 230 extends between runners 226A and 226B at a forward end thereof. A wheel 224 downwardly projects from each opposing end of each runner 226A and 226B. Frame assembly 222 comprises a plurality of spaced apart vertical risers 232 having a plurality of lateral supports 234 extending therebetween. A horizontal platform 236 is mounted on frame assembly 222 forward of and at an elevation above first cross member 228. A pair of spaced apart hand rails 238A and 238B extend from corresponding runner 226A and 226B and connect with frame assembly 222.

Figure 8:
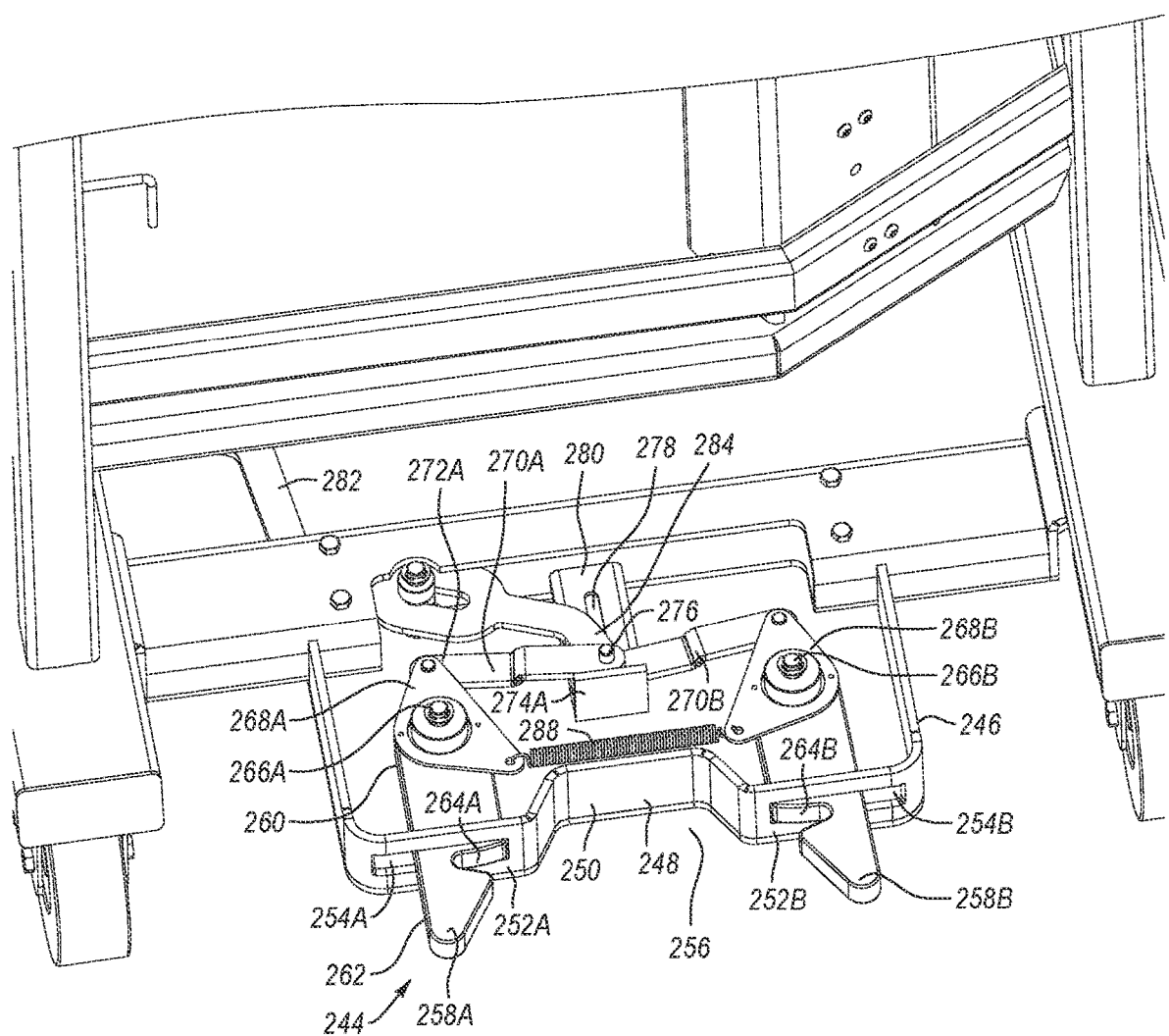
FIG. 8 is a top perspective view of the locking assembly shown in FIG. 7.

Mounted on second cross member 230 of base 220 is a locking assembly 244. Locking assembly 244 comprises a housing 246 having a front face 248. As depicted in FIG. 8, front face 248 comprises an outwardly flaring, substantially U-shaped receiver 250 having end faces 252A and 252B extending from the opposing ends thereof. Access slots 254A and 254B are formed on end faces 252A and 252B, respectively. Receiver 250 bounds a recess 256 of complimentary shape that is configured to receive face plate 202. Locking assembly 244 further comprises a pair of engaging arms 258A and 258B. Each arm 258A and 258B has a first end 260 disposed within housing 246 and an opposing second end 262 that projects out through a corresponding access slot 254. Engaging arms 258A and 258B have a notch 264A and 264B, respectively, that are opposingly facing.

Engaging arms 258A and 258B can be movably positioned between a locking position as shown in FIG. 8 wherein second end 262 of arms 258 pivot towards each other and a release position wherein second end 262 of engaging arms 258 are pivoted away from each other. A mechanical assembly is used for moving engaging arms 258 between the two positions. The mechanical assembly includes an axel 266A secured to housing 246 and extending through first end 260 of engaging arm 258A so that engaging arm 258A can pivot about axel 266A. A pivot plate 268A is secured to first end 260 of engaging arm 258A so as to also pivot about axel 266A. A linkage 270A has a first end 272A pivotally mounted to pivot plate 268A and an opposing second end 274A mounted to a guide pin 276. Guide pin 276 can pivot within and slide along a guide slot 278 that is formed on a bracket 280. Bracket 280 is secured to housing 246. A corresponding axel 266B, pivot plate 268B, and linkage 270B are similarly coupled with engaging arm 258B. A lever 282 is pivotally mounted to housing 246 or base 220 and includes a first end 284 coupled with guide pin 276 and an opposing second end 286 (FIG. 7). As a result of the mechanical linkage, manual manipulation of second end 286 of lever 282 pivots engaging arms 258A and 258B between the locking and release positions. Finally, locking assembly 244 also includes a spring 288 resiliently extending between pivot plates 268A and 268B a location forward of axels 266A and 266B. As a result of this configuration, spring 288 functions to resiliently pivot second end 262 of engaging arms 258A and 258B towards each other.

During use, it is desirable to engage locking assembly 244 with locking catch 200 so that container station 14 is rigidly locked with docking station 12. This is accomplished by advancing locking catch 200 into recess 256 of locking assembly 244. Locking catch 200 has a configuration complimentary to and is configured to nest within recess 256 so that the structures are self aligning as they couple together. As locking catch 200 advances into recess 256, engagement rods 210 strike against the inside face of engagement arms 258A and 258B, respectively. Because of the inward sloping of the faces, engagement arms 258A and 258B resiliently flex outward against the resistant spring 288 as engagement rods 210 are advanced forward.

Finally, once engagement rods 210 are advanced to notches 264A and 264B, engagement arms 258 resiliently pivot inward thereby retaining engagements rods 210A and 210B within notches 264A and 264B. In this position, container station 14 is rigidly secured to docking station 12. As discussed below in greater detail, in this position, docking station 12 can be used to facilitate mixing and other processing of fluid within container assembly 16. When it is desired to separate container station 14 from docking station 12, lever 282 is moved so that engagement arms 258 are spread apart into the release position thereby releasing engagement with locking catch 200. It is appreciated that there are a variety of different types of locking systems that can be used for removably securing container station 14 to docking station 12.

Figure 9:
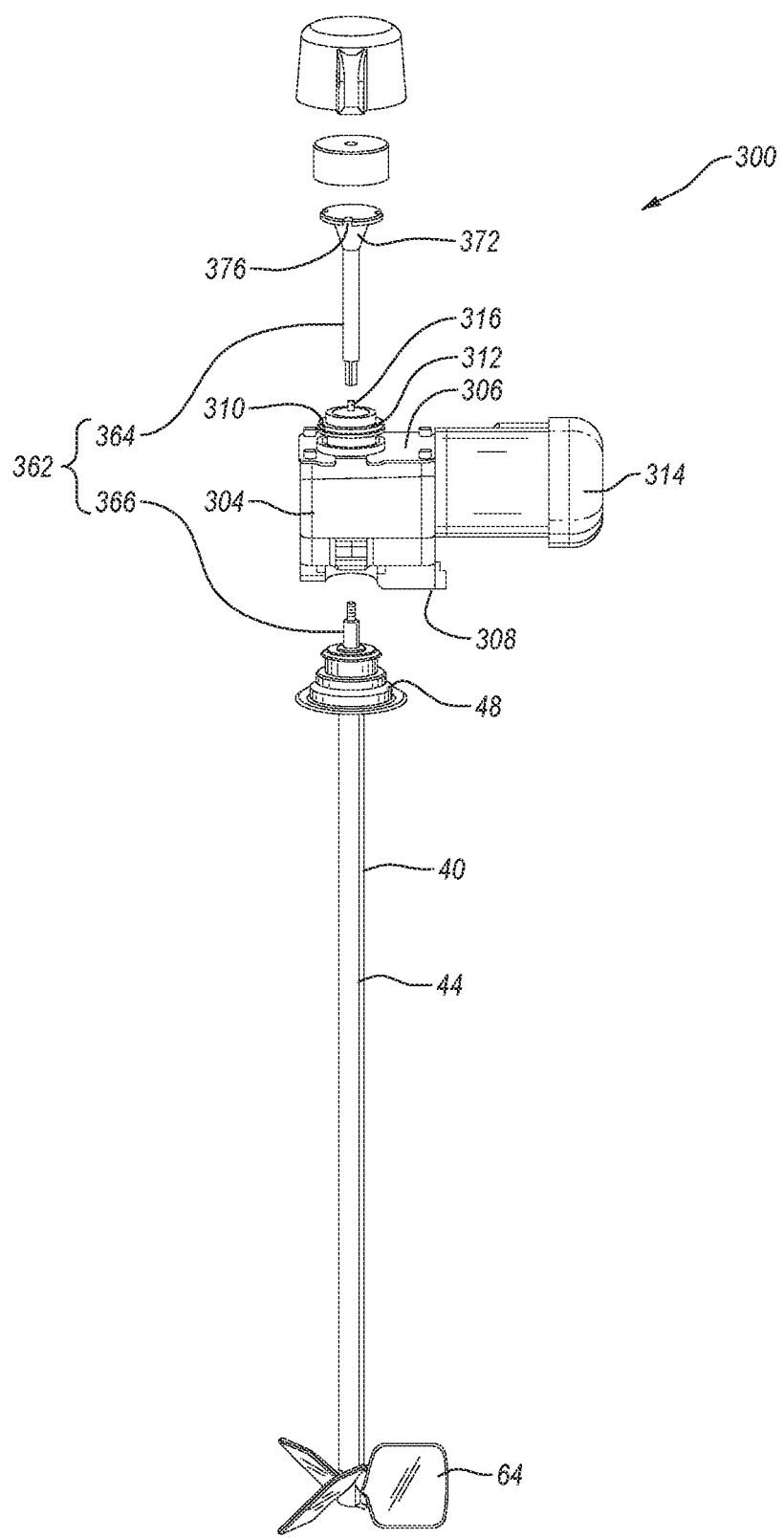
FIG. 9 is a partially disassembled perspective view of a drive motor assembly of the docking station shown in FIG. 7 in association with the impeller assembly and drive shaft.

Returning to FIG. 7, docking station 12 further comprises a drive motor assembly 300 coupled with stand 218 by an adjustable arm assembly 302. Drive motor assembly 300 is used in conjunction with drive shaft 362 (FIG. 3) and can be used for mixing and/or suspending a culture or other solution within container 18 (FIG. 2). Turning to FIG. 9, drive motor assembly 300 comprises a housing 304 having a top surface 306 and an opposing bottom surface 308. An opening 310 extends through housing 304 from top surface 306 to bottom surface 308. A tubular motor mount 312 is rotatably secured within opening 310 of housing 304. Upstanding from motor mount 312 is a locking pin 316. A drive motor 314 is mounted to housing 304 and engages with motor mount 312 so as to facilitate select rotation of motor mount 312 relative to housing 304. Drive shaft 362 is configured to pass through motor mount 312 so that engaging portion 372 of drive shaft 362 is retained within motor mount 312 and locking pin 316 of motor mount 312 is received within notch 376 of drive shaft 362. As a result, rotation of motor mount 312 by drive motor 314 facilitates rotation of drive shaft 362. Further discussion of drive motor assembly 300 and how it engages with drive shaft 362 and alternative designs of drive motor assembly 300 are discussed in US Patent Publication No. 2011/0188928 which was previously incorporated herein by specific reference.

Figure 10:
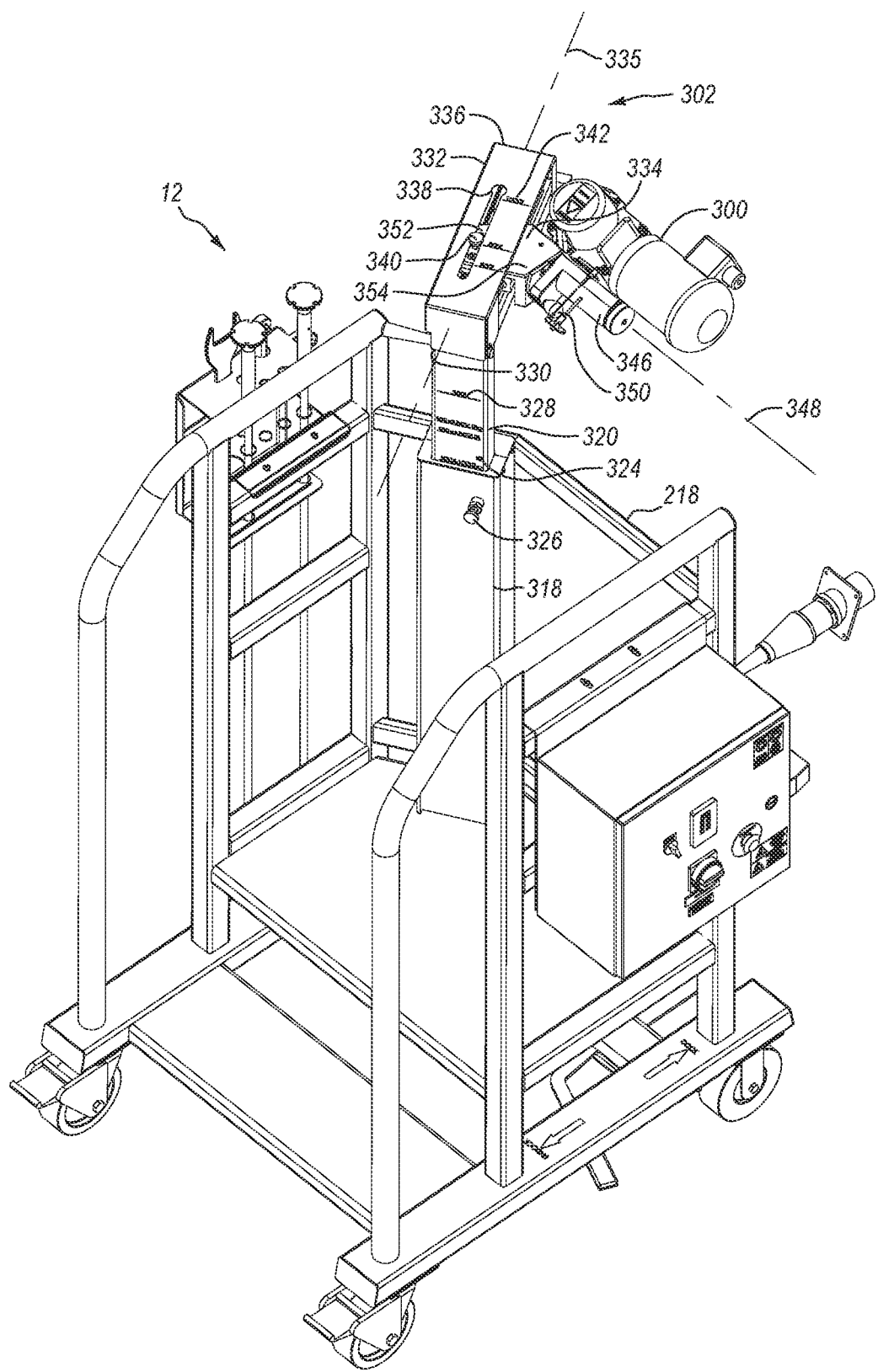
FIG. 10 is a top perspective view of the docking station shown in FIG. 7.
Figure 11:
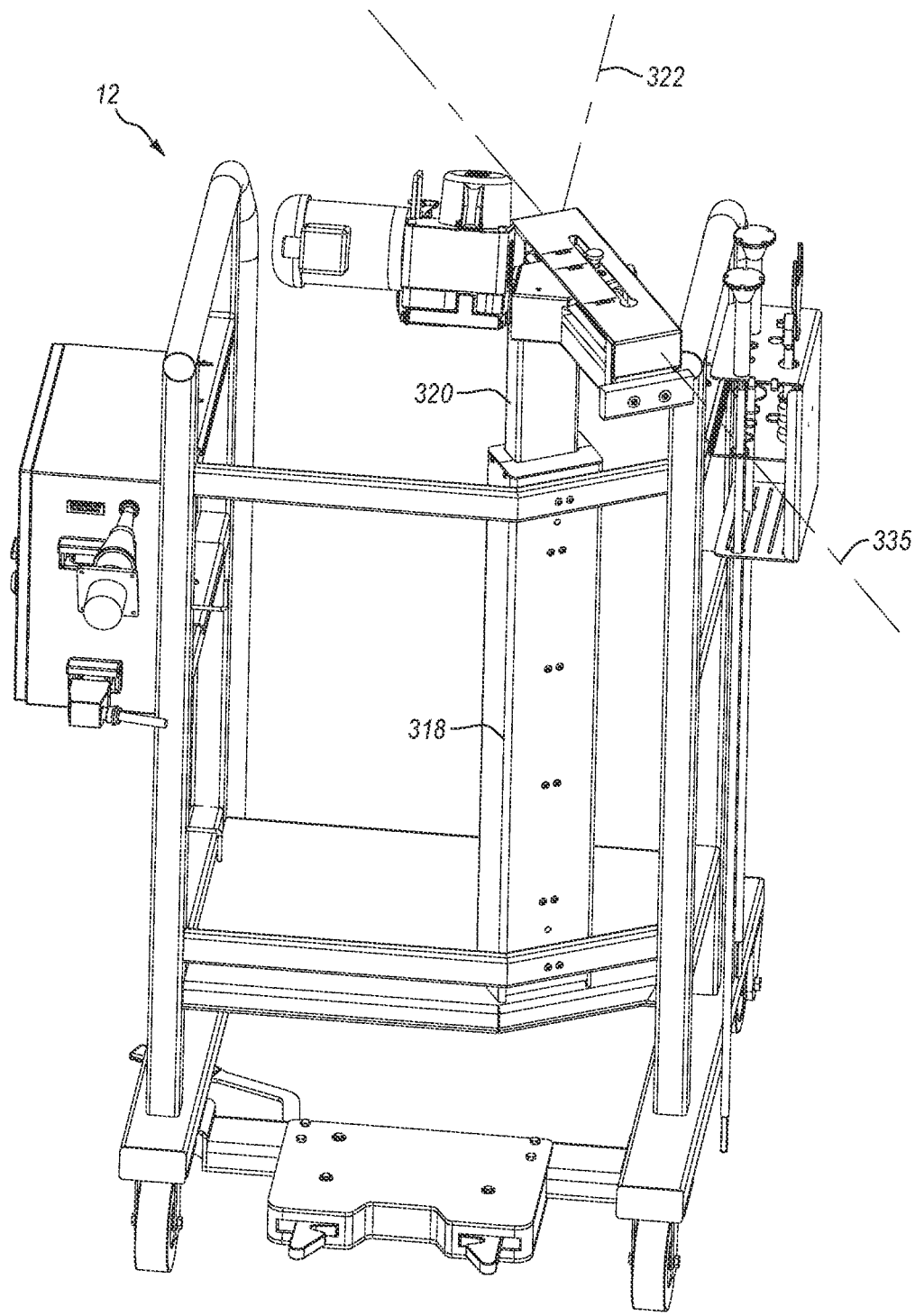
FIG. 11 is an alternative perspective view of the docking station shown in FIG. 7.

Arm assembly 302 is used to adjust the position of drive motor assembly 300 and thereby also adjust the position of drive shaft 362. As depicted in FIG. 10, arm assembly 302 comprises a first housing 318 that is rigidly secured to stand 218. Slidably disposed within first housing 318 is an elongated first support 320. First housing 318 and first support 320 are orientated such that first support 320 can slide vertically up and down along a first axis 322 (FIG. 11). In one embodiment, axis 322 can extend orthogonally to a horizontal surface on which docking station 12 is disposed. In alternative embodiments, first housing 318 and first support 320 can be disposed so that axis 322 is disposed at an angle in a range between 0° to about 30° relative to a horizontal surface. Other angles can also be used.

In one embodiment of the present invention, means are provided for selectively locking first support 320 to first housing 318 at different locations along axis 322. In one embodiment of the present invention, such means comprises holes 324 formed at spaced apart locations along first support 320 and a spring activated pin 326 mounted to first housing 318. By pulling out pin 326, first support 320 is free to slide vertically up and down along axis 322. By pushing the pin 326 in, pin 326 is received within a corresponding hole 324 so as to lock first support 320 in place. It is appreciated that any number of conventional clamps, pins, screws, latches, fasteners, or the like can be used for securing first support 320 to first housing 318. Indicia or markings 328 can be formed along the surface of first support 320 to indicate the relative position of first support 320.

First support 320 terminates at an upper end 330. Mounted on upper end 330 is a second housing 332. A second support 334 has a first end 352 and an opposing second end 354. First end 352 is slidably mounted on second housing 332 so that second support 334 can be positioned at various locations along a second axis 335. Second support 334 and second housing 332 are typically disposed so that second axis 335 is horizontally disposed and is orthogonal to first axis 322. In alternative embodiments, however, second axis 335 can be disposed at an angle in a range between 0° to about 30° relative to first axis 322. Other angles can also be used.

Rails are typically disposed within second housing 332 on which second support 334 slides. In alternative embodiments, a variety of alternative mechanism can be used to permit second support 334 to slide relative to second housing 332. In one embodiment of the present invention, means are provided for selectively locking second support 334 at different locations along second housing 332. By way of example and not by limitation, second housing 332 is shown having a top surface 336 having an elongated slot 338 formed along the length thereof. A spring actuated pin is disposed within slot 338 and extends through second support 334. A plurality of spaced apart holes are formed on the bottom surface of second housing 332 or along the rails or other structures disposed within second house 332. During use, when pin 340 is elevated, second support 334 is free to slide back and forth along second housing 332 along second axis 335. When pin 340 is pressed down, pin 340 is received within a hole to thereby lock pin 340 and second support 334 in place. Indicia 342 can be disposed on top surface 336 to identify predefined locations for second support 344.

A third support 346 is rotatably mounted to second end 354 of second support 334. Third support 346 is mounted so that it rotates about a third axis 348. Third axis 348 can be disposed in a horizontal plane and or in the same plane as second axis 335. Third axis can also be disposed at an angle in a range between about 0° to about 30° relative to second axis 335. Drive motor assembly 300 is secured to third support 346 such that rotation of third support 346 facilitates concurrent rotation of drive motor assembly 300.

One embodiment of the present invention also includes means for locking third support 346 at different angles about third axis 348. By way of example and not by limitation, a spring activated pin 350 is mounted on third support 346. When pin 350 is retracted, third support 346 is free to rotate about third axis 348. As pin 350 is advanced inward, it is received within one of a plurality of holes formed on second end 354 of second support 334. As a result, third support 346 is thereby precluded from further rotation. Other conventional fastening techniques can also be used.

In view of the foregoing, first support 320 can facilitate vertical movement of drive motor assembly 300, second support 334 can facilitate horizontal movement of drive motor assembly 300 and third support 346 can facilitate rotational movement of drive motor assembly 300. As a result, arm assembly 302 can be used to position drive motor assembly 300 and drive shaft 362 which extends there through in a variety of different locations and orientations. As a result, arm assembly 302 enables docking system station 12 to be used with a variety of different sized and shaped container stations 14.

Figure 12:
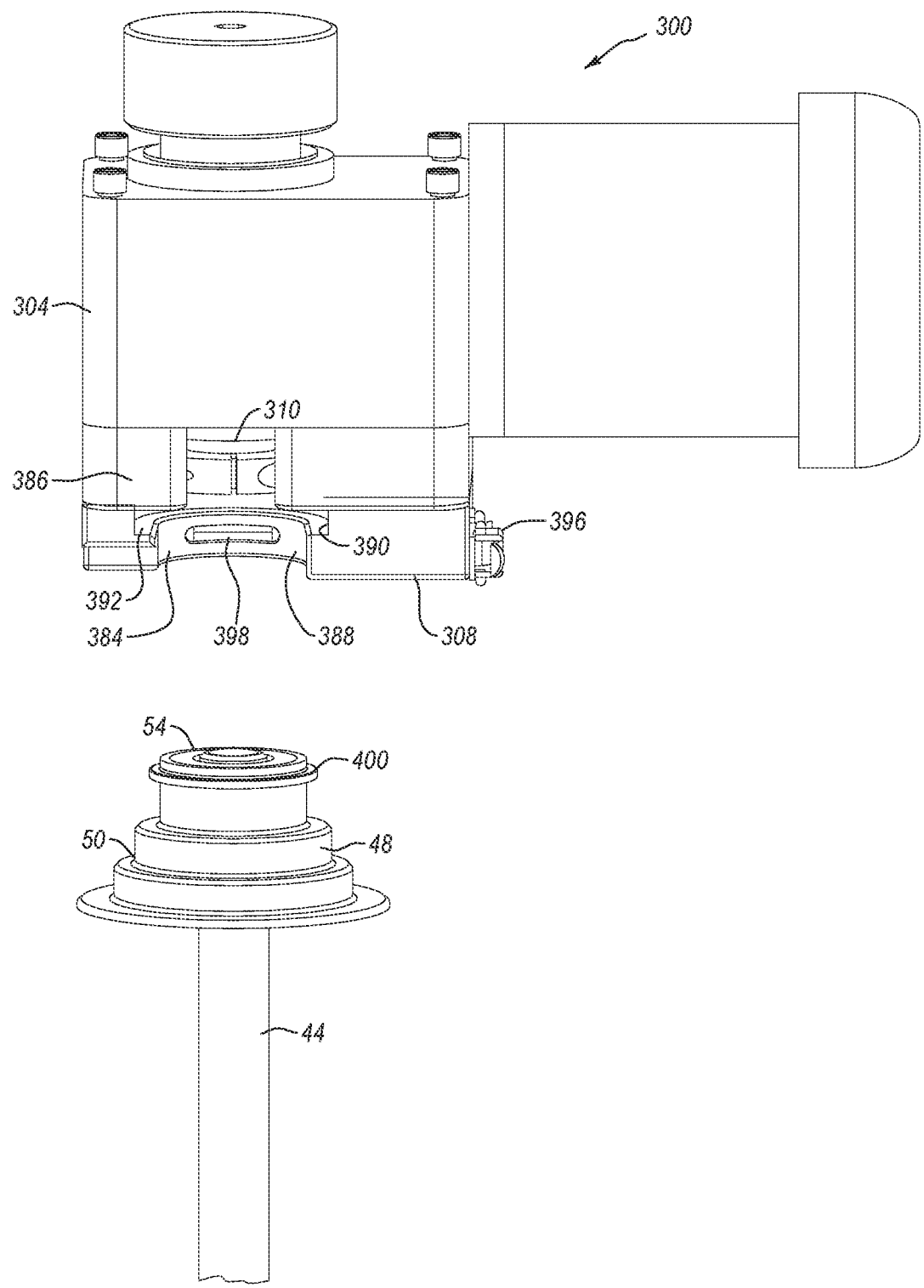
FIG. 12 is a front perspective view of the drive motor assembly and rotational assembly.

During use, container station 14 is wheeled to docking station 12 and/or docking station 12 is wheeled to container station 14 and the two are securely coupled together, as shown in FIG. 1, by engaging locking assembly 244 (FIG. 7) with catch 200 (FIG. 4). In this secure position, arm assembly 302 is used to properly position drive motor assembly 300 so that rotational assembly 48 (FIG. 2) can be coupled with drive motor assembly 300. Specifically, as depicted in FIG. 12, housing 304 of drive motor assembly 300 has an open access 384 that is recessed on a front face 386 so as to communicate with opening 310 extending through housing 304. Access 384 is in part bounded by a substantially C-shaped first side wall 388 that extends up from bottom surface 308, a concentrically disposed substantially C-shaped second side wall 390 disposed above first side wall 388 and having a diameter larger than first side wall 388, and a substantially C-shaped shoulder 392 extending between side walls 388 and 390. As shown in FIG. 2, a door 394 is hingedly mounted to housing 304 and selectively closes the opening to access 384 from front face 386. Returning to FIG. 12, door 394 is secured in a closed position by a latch 396. Positioned on first side wall 388 is a section 398 of a resilient and/or elastomeric material such as silicone. Other sections 398 of similar materials can also be positioned on first side wall 388 or the interior surface of door 394.

Figure 13:
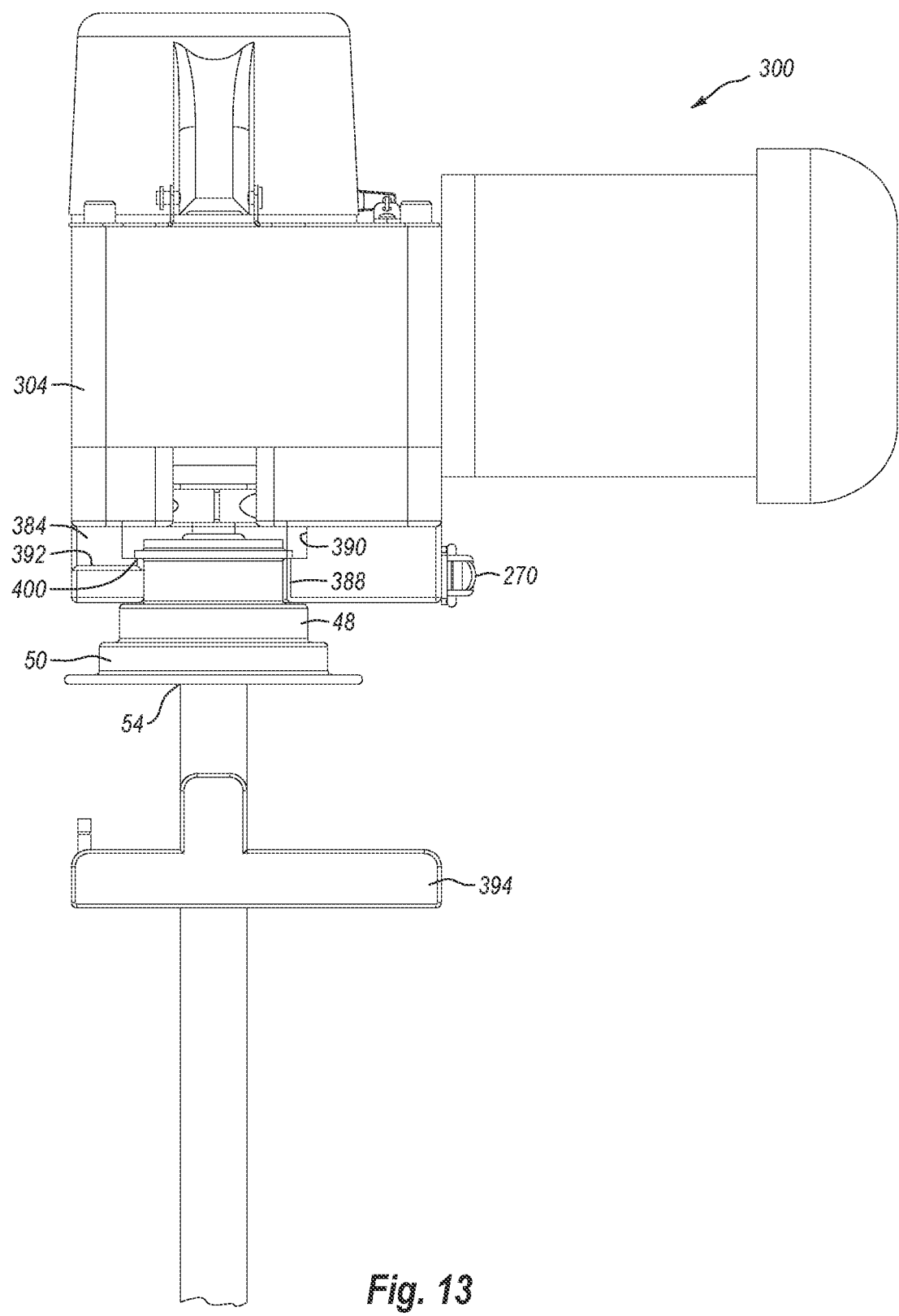
FIG. 13 is an elevated front view of the rotational assembly shown in FIG. 12 coupled with the drive motor assembly.

As depicted in FIG. 13, to facilitate attachment of rotational assembly 48 to housing 304, with door 394 rotated to an open position, rotational assembly 48 is horizontally slid into access 384 from front face 386 of housing 304 so that a support flange 400 radially outwardly extending from an upper end of rotational assembly 48 rests on shoulder 392 of access 384. Rotational assembly 48 is advanced into access 384 so that the passage extending through hub 54 of rotational assembly 48 aligns with the passage extending through motor mount 312 (FIG. 9). In this position, door 394 is moved to the closed position and secured in the closed position by latch 396. As door 394 is closed, casing 50 of rotational assembly 48 is biased against the one or more sections 398 (FIG. 12) of resilient material so as to clamp rotational assembly 48 within access 384 and thereby prevent unwanted rotational movement of casing 50 relative to housing 304 of drive motor assembly 300.

Once rotational assembly 48 is secured to drive motor assembly 300, drive shaft 362 can be advanced down through drive motor assembly 300 and into impeller assembly 40 so as to engage impeller 64. Once drive shaft 362 is properly positioned, drive motor assembly 300 is activated causing drive shaft 362 to rotate impeller 64 and thereby mix or suspend the fluid within container 18. When the processing is complete, drive shaft 362 is removed and rotational assembly 48 is separated from drive motor assembly 300. Container station 14 can then be separated from docking station 12 by releasing catch 200 from locking assembly 244. A second container station 14 can then be couple with docking station 12 in the same manner as discussed above. Where the second container station 14 is a different size or configuration or where the container assembly 16 coupled thereto is a different size or configuration, arm assembly 302 can be used to properly position drive motor assembly 300 at a potentially different location so that the new rotational assembly 48 can be coupled with drive motor assembly 300. Drive shaft 362 can then again be advanced down through drive motor assembly 300 and into impeller assembly 40 of the new container assembly 16.

In view of the foregoing, it is appreciated that a single docking station 14 can be used with a variety of different container stations 14 and/or container assemblies 16 wherein the different container stations 14 and/or container assemblies 16 can be of different size and/or shape.

Figure 14:
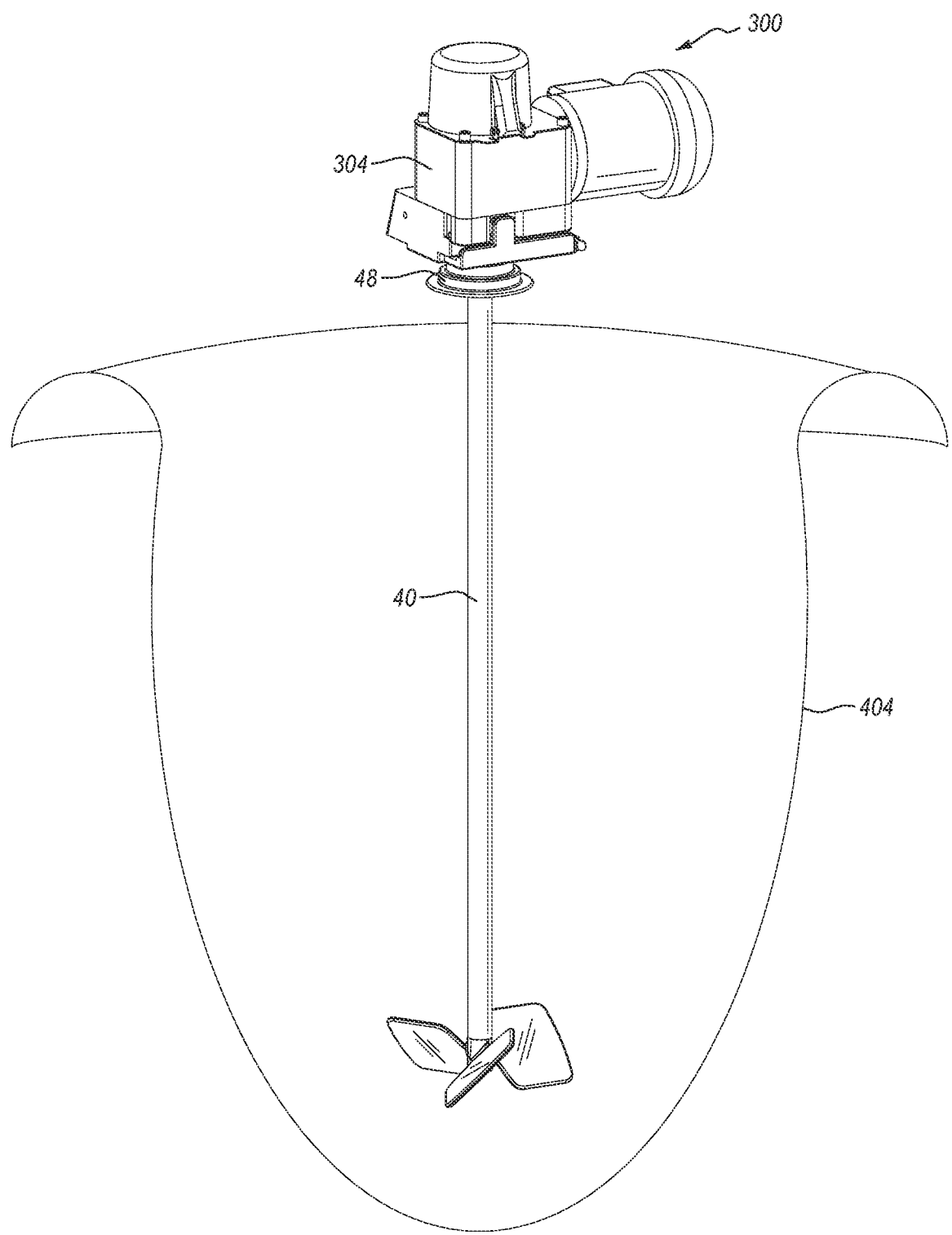
FIG. 14 is a perspective view of an alternative embodiment of a container being used with a drive motor assembly and impeller assembly.
Figure 15:
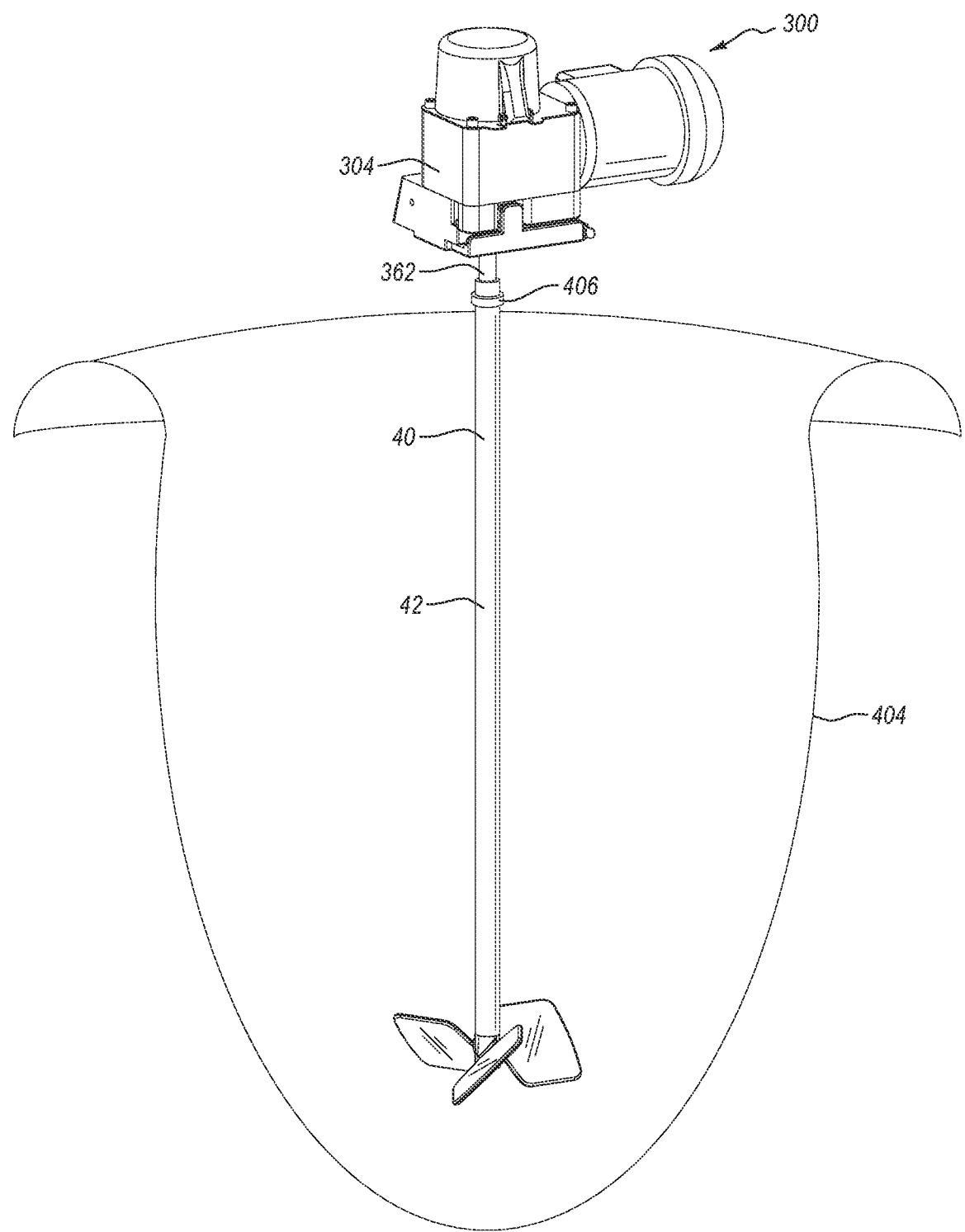
FIG. 15 is a perspective view of an alternative embodiment of the impeller assembly shown in FIG. 14.

Depicted in FIG. 14 is an alternative embodiment of the present invention. In this embodiment drive motor assembly 300 operates with a container 404 that is an open top liner. Container 404 is positioned within chamber 92 of support housing 78 so that is drapes over annular lip 94 (FIG. 1). This configuration can be used as a lower cost alternative for mixing non-sterile fluids. In this embodiment, rotational assembly 48 merely functions to secure impeller assembly 40 to drive motor assembly 300 so that it does not unintentionally slide off of drive shaft 362. In alternative embodiments, because rotational assembly 48 is no longer forming a sealed fluid connection with the container, rotational assembly 48 can be substantially simplified. For example, as shown in FIG. 15, rotational assembly 48 can be replaced by a clamp 406 that secures tubular connector 42 to drive shaft 362. Further alternative embodiments with regard to impeller assembly 40 and how they can be attached to drive motor assembly 300 or drive shaft 362 are discussed in US Patent Publication No. 2011/0188928 which was previously incorporated herein by specific reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tube management system comprising:
    a rack extending between a first end and an opposing second end, the rack disposed within a door of a support housing of a container station;
    an elongated first shaft having a first end and an opposing second end, the first shaft being secured to the rack;
    a securing structure secured to the first shaft;
    a collapsible bag bounding a chamber, the collapsible bag disposed within the container station; and
    a tubular member projecting from the collapsible bag and extending through the door of the support housing,
    wherein the securing structure at least partially encircles the tubular member.

2. The tube management system as recited in claim 1, wherein the securing structure is secured at or toward the second end of the first shaft, the securing structure outwardly projecting away from the first shaft.

3. The tube management system as recited in claim 1, wherein first shaft has a central longitudinal axis extending between the first end and the second end thereof, the securing structure outwardly projecting from the first shaft so as to extend orthogonal to the central longitudinal axis.

4. The tube management system as recited in claim 1, wherein the securing structure has a bend.

5. The tube management system as recited in claim 1, wherein the securing structure is resiliently flexible.

6. The tube management system as recited in claim 1, wherein a portion of the securing structure is annular.

7. The tube management system as recited in claim 1, wherein the securing structure has a first end that at least partially encircles first shaft.

8. The tube management system as recited in claim 1, wherein the first end of the first shaft is removably secured to the rack and the securing structure is secured to the second end of the first shaft.

9. The tube management system as recited in claim 1, wherein the rack comprises a flat plate.

10. The tube management system as recited in claim 1, wherein the rack has a face extending between the first end of the rack and the second end of the rack, the first shaft projecting orthogonal to the face of the rack.

11. The tube management system as recited in claim 1, further comprising an elongated second shaft having a first end and an opposing second end, the second shaft being secured to the rack at a location spaced apart from the first shaft.

12. The tube management system as recited in claim 11, further comprising an elongated third shaft having a first end and an opposing second end, the third shaft being secured to the rack at a location spaced apart from the first shaft and the second shaft.

13. The tube management system as recited in claim 1, wherein the tubular member comprises a tube.

14. The tube management system as recited in claim 1, further comprising a rotatable impeller disposed within the chamber of the collapsible bag.

15. The tube management system as recited in claim 1, wherein the rack is U-shaped.

16. The tube management system as recited in claim 1, wherein the support housing has a floor and an upstanding sidewall, the collapsible bag being disposed on the floor and the rack being secured to the sidewall.

17. The tube management system as recited in claim 1, wherein the securing structure is disposed directly against the tubular member.

18. The tube management system as recited in claim 1, wherein the securing structure is a clamp.

\* \* \* \* \*